(12) United States Patent
Keller et al.

(10) Patent No.: US 10,131,482 B2
(45) Date of Patent: Nov. 20, 2018

(54) ANTIMICROBIAL PACKAGING MATERIAL

(71) Applicant: Graphic Packaging International, Inc., Atlanta, GA (US)

(72) Inventors: Samuel F. Keller, West Monroe, LA (US); Alan Fontaine, Louisville, CO (US)

(73) Assignee: Graphic Packaging International, LLC, Atlanta, GA (US)

( * ) Notice: Subject to any disclaimer, the term of this patent is extended or adjusted under 35 U.S.C. 154(b) by 0 days.

(21) Appl. No.: 14/331,439

(22) Filed: Jul. 15, 2014

(65) Prior Publication Data

US 2015/0024094 A1    Jan. 22, 2015

Related U.S. Application Data

(60) Provisional application No. 61/846,960, filed on Jul. 16, 2013.

(51) Int. Cl.
    *B65D 81/28*     (2006.01)
    *A01N 25/34*     (2006.01)
    (Continued)

(52) U.S. Cl.
    CPC .............. *B65D 81/28* (2013.01); *A01N 43/80* (2013.01); *A01N 59/20* (2013.01); *B65D 81/24* (2013.01);
    (Continued)

(58) Field of Classification Search
    CPC ........ B65D 81/28; A01N 25/10; A01N 59/20; A01N 43/80; A01N 25/34; D21H 5/22;
    (Continued)

(56) References Cited

U.S. PATENT DOCUMENTS 4,574,978 A * 3/1986 Hodges ..................... B65F 1/06
                                                         206/427
5,480,718 A * 1/1996 Shigemoto et al. ......... 428/34.2
(Continued)

FOREIGN PATENT DOCUMENTS

CN     102 517 993 A    6/2012
EP      0 750 853 A2     1/1997
(Continued)

OTHER PUBLICATIONS

International Search Report and Written Opinion for PCT/US2014/046613 dated Nov. 4, 2014.
(Continued)

*Primary Examiner* — Christopher Demeree
(74) *Attorney, Agent, or Firm* — Womble Bond Dickinson (US) LLP

(57) ABSTRACT

A packaging material includes an antimicrobial agent adhered to a substrate. The antimicrobial agent can include copper, and the packaging material can include cellulose. The substrate can be paperboard, and the copper can be a copper salt, such as copper sulfate. The packaging material may be provided by causing adherence between the substrate and the antimicrobial agent, such as by coating the substrate with the antimicrobial agent. Then, the packaging material may be cut into sheets. The sheets may be formed into cartons or other suitable packages.

21 Claims, 2 Drawing Sheets

(51) Int. Cl.
*A01N 43/80* (2006.01)
*A01N 25/10* (2006.01)
*A01N 59/20* (2006.01)
*B65D 81/24* (2006.01)

(52) U.S. Cl.
CPC ............... *Y10T 428/31971* (2015.04); *Y10T 428/31996* (2015.04)

(58) Field of Classification Search
CPC ........ D21H 19/00; D21H 19/10; D21H 19/12; D21H 19/14; D21H 19/16; D21H 19/18; D21H 19/20; D21H 19/22; D21H 19/24; D21H 19/26; D21H 19/28; D21H 19/30; D21H 19/32; D21H 19/34
USPC .......................... 229/103.2, 5.81; 428/537.5
See application file for complete search history.

(56) References Cited

U.S. PATENT DOCUMENTS

| | | | |
|---|---|---|---|
| 5,508,072 A * | 4/1996 | Andersen et al. | 428/34.5 |
| 5,693,384 A * | 12/1997 | Hollinger, Jr. | 428/34.2 |
| 6,541,560 B1 | 4/2003 | Rozynov et al. | |
| 6,919,111 B2 * | 7/2005 | Swoboda et al. | 428/34.2 |
| 7,014,909 B2 | 3/2006 | Rozynov et al. | |
| 7,311,933 B2 * | 12/2007 | Bringley | B65D 81/28 426/124 |
| 2005/0227895 A1 * | 10/2005 | Ghosh et al. | 510/383 |
| 2005/0228351 A1 | 10/2005 | Bruno et al. | |
| 2008/0096449 A1 | 4/2008 | Bruno et al. | |
| 2010/0077529 A1 * | 4/2010 | Stone et al. | 2/85 |
| 2010/0187295 A1 * | 7/2010 | Spivey, Sr. | B65D 71/36 229/120.38 |
| 2010/0263793 A1 * | 10/2010 | Ylitalo et al. | 156/344 |

FOREIGN PATENT DOCUMENTS

| | | |
|---|---|---|
| EP | 1 120 040 A2 | 8/2001 |
| JP | 03-148470 A | 6/1991 |
| JP | 05-124676 A | 5/1993 |
| JP | 2001-288697 A | 10/2001 |
| JP | 2008-088593 A | 4/2008 |
| WO | WO 03/104557 A2 | 12/2003 |

OTHER PUBLICATIONS

Borkow et al., "Copper as a Biocidal Tool," Current Medicinal Chemistry, vol. 12, No. 18, Aug. 1, 2005, pp. 2163-2175.
Supplementary European Search Report for EP 14 82 6256 dated Oct. 31, 2016.

* cited by examiner

ANTIMICROBIAL PACKAGING MATERIAL

CROSS-REFERENCE TO RELATED APPLICATION

This application claims the benefit of U.S. Provisional Application No. 61/846,960, filed Jul. 16, 2013, the entire contents of which are incorporated herein by reference.

BACKGROUND

It is common for packages, such as cartons and bags, to be made of paper-based packaging materials, and for the packages to contain food products. As another example, one or more pieces of wrapping paper may be wrapped around a food product to form a package. Each food product may be contained solely in a package formed of paper-based packaging material; or the food product may be contained in an inner container, and the inner container may be contained in an outer package formed of paper-based packaging material.

When paper-based packaging materials are in direct contact with food or other products that may promote the growth of microorganisms, in some circumstances microorganisms may undesirably grow on packaging material. For example, a beverage may unintentionally leaking from an inner container that is positioned within an outer package of paper-based packaging material.

Antimicrobial packaging materials inhibit the growth of microorganisms. There is a desire for antimicrobial packaging materials that provide a new balance of properties.

BRIEF SUMMARY

In accordance with one aspect of this disclosure, a packaging material comprises an antimicrobial agent adhered to a substrate, wherein the antimicrobial agent may comprise copper, and the packaging material may comprise cellulose. More specifically, the substrate may be, or may include, paperboard and/or any other suitable material(s), such as paper-based material(s). Accordingly, the packaging material may be configured as a carton blank. In one example, the copper comprises a copper salt, and the copper salt may comprise copper sulfate. In one embodiment, the antimicrobial agent is in the form of, or part of, a coating that at least partially covers the substrate, such as by at least partially covering an inner surface of the substrate. The packaging material may be configured as a package, wherein the packaging material may extend at least partially around an interior space of the package. The package may be a carton, and one or more containers, articles or other contents may be at least partially contained in the interior space of the carton.

In one aspect of this disclosure, a method comprises at least partially providing a packaging material, and the method may include causing adherence between a substrate and an antimicrobial agent, so that the packaging material comprises the antimicrobial agent adhered to the substrate. The substrate may comprise cellulose, the antimicrobial agent may comprise copper, and/or the method may be characterized by other of the above-discussed features. In one embodiment, the substrate is coated with the antimicrobial agent or a substance containing the antimicrobial agent. As one example, the coating may be in the form of an ink that includes the antimicrobial agent, and the ink may be printed onto the substrate. Thereafter, the packaging material may be cut into sheets (e.g., formed into blanks). The sheets may be formed into packages, such as, but not limited to, cartons.

The foregoing presents a simplified summary of some aspects of this disclosure in order to provide a basic understanding. The foregoing is not an extensive summary and is not intended to identify key or critical elements of the invention or to delineate the scope of the invention. The purpose of the foregoing summary is to present some concepts of this disclosure in a simplified form as a prelude to the more detailed description that is presented later. For example, other aspects will become apparent from the following.

BRIEF DESCRIPTION OF THE DRAWINGS

In the following, reference is made to the accompanying drawings, which are not necessarily drawn to scale and may be schematic. The drawings are exemplary only, and should not be construed as limiting the inventions.

DETAILED DESCRIPTION

Exemplary embodiments are described below and illustrated in the accompanying drawings, in which like numerals refer to like parts throughout the several views. The embodiments described provide examples and should not be interpreted as limiting the scope of the invention. Other embodiments, and modifications and improvements of the described embodiments, will occur to those skilled in the art and all such other embodiments, modifications and improvements are within the scope of the present invention. For example, features illustrated or described as part of one embodiment can be used in the context of another embodiment to yield a further embodiment, and these further embodiments are within the scope of the present invention.

An aspect of a first embodiment of this disclosure is the provision of an antimicrobial treatment (e.g., anti-fungal treatment) for packaging materials (e.g., paperboard, and carton blanks and cartons formed therefrom). Other aspects relate to a method of treating packaging materials with the antimicrobial treatment, and packaging materials that have been treated with the antimicrobial treatment.

In accordance with the first embodiment, copper-based materials, such as, but not limited to, copper salts (e.g. copper sulfate) may be used alone, or in combination with other inorganic salts and/or organic biocides, to inhibit microbiological growth (e.g., fungal or bacterial) in paper-based packaging materials (e.g., paper or paperboard). More specifically, an anti-microbial material in the form of, or including, copper salt(s) may be incorporated into paper and paperboard-based packaging materials and packages. The copper salt(s) may be incorporated alone or in combination with other materials. For example, the other materials may be one or more inorganic materials, such as calcium hydroxide, and/or one or more organic biocides, such as isothiazolone. The antimicrobial treatment comprising copper salt(s)

seeks to be relatively low cost, highly effective, and stable (e.g., it may not degrade in the same way that many organic biocides degrade).

Figure 1:
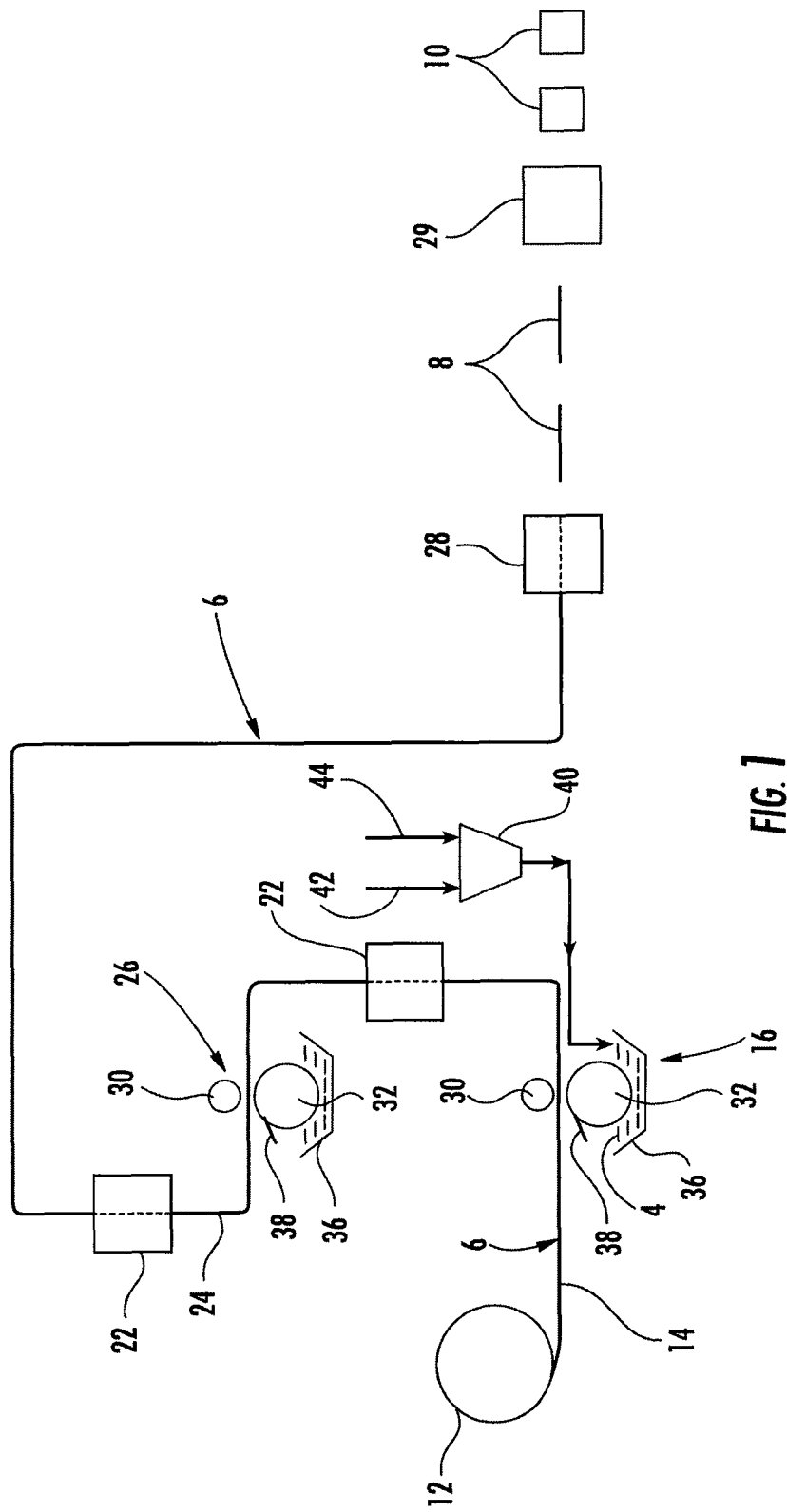
FIG. 1 schematically illustrates a system and method for applying at least an antimicrobial treatment to packaging material, and then converting the treated packaging material into carton blanks and cartons, in accordance with a first embodiment of this disclosure.

FIG. 1 schematically illustrates a system and method for applying at least an antimicrobial treatment 4 to a web 6 of packaging material, and then converting the treated packaging material into sheets 8 that may be formed into packages 10, in accordance with the first embodiment of this disclosure. In the first embodiment, the antimicrobial treatment 4 is applied to the web 6 of packaging material after the web has been fully formed and dried in a papermaking machine (not shown). The web 6 of packaging material may be more generally referred to as a substrate and/or the web 6 may comprise, consist of, or consist essentially of the substrate, as discussed in greater detail below.

In the following, first an overview is provided for the system and method of the first embodiment, and thereafter selected aspects of the first embodiment are discussed in greater detail. Thereafter, other embodiments are discussed, in which the antimicrobial treatment 4 may be associated with a precursor of the web 6, such as in a papermaking machine (not shown).

As shown in FIG. 1, the web 6 of packaging material is drawn from a roll 12. Then, adherence is caused between the web 6 (e.g., substrate) and an antimicrobial agent 44, which may be a solute. More specifically, the antimicrobial agent 44 may be part of the liquid antimicrobial treatment 4, and the backside 14 of the web 6 may be coated with at least the liquid antimicrobial treatment. This coating of the backside 14 may be facilitated by drawing the web 6 past or through at least one backside coater 16. In the first embodiment, the backside 14 of the web 6 is that side of the web that will ultimately be the interior surface of packages 10 (e.g., see the carton 10 of FIG. 3) formed from sheets 8 of the treated packaging material (e.g., see the blank 8 of FIG. 2) cut from the web. Depending upon the type of any solvent in the liquid antimicrobial treatment 4 and/or other factors, the treated backside 14 of the web 6 may be dried, such as by drawing the web through at least one conventional dryer 22 (e.g., heater) or other suitable curing device.

Similarly, one or more front coatings may optionally be applied to the front side 24 of the web 6. The front coating(s) may be facilitated by drawing the web 6 past or through at least one front coater 26. In the first embodiment, the front side 24 will ultimately be the exterior surface of the packages 10 (e.g., see the carton 10 of FIG. 3) formed from sheets 8 of the treated packaging material (e.g., see the blank 8 of FIG. 2) cut from the web 6. Depending upon the type of any solvents in the front coating(s) and/or other factors, the front side 24 may be dried, such as by drawing the web 6 through at least one conventional dryer 22 (e.g., heater) or other suitable curing device.

Figure 2:
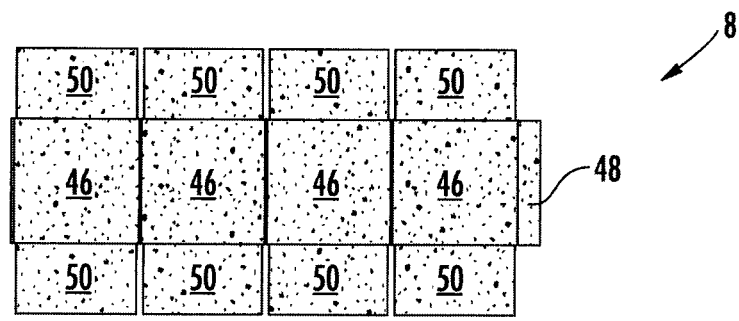
FIG. 2 schematically illustrates an interior side of a carton blank provided by the system of FIG. 1, in accordance with the first embodiment.

Thereafter, and optionally after winding and unwinding the treated web 6, the treated web may be provided to at least one conventional converter 28 for operating in a conventional manner to serially form the treated web into the individual sheets 8 of the treated packaging material. For example, FIG. 2 illustrates that each of the sheets 8 may be in the form a carton blank. Thereafter, the individual sheets 8 of the treated packaging material may be provided to at least one conventional packaging-forming machine 29 (FIG. 1) for operating in a conventional manner to serially form the sheets 8 into the packages 10.

With continued reference to FIG. 1, selected aspects of the first embodiment are discussed in greater detail in the following. The substrate or web 6 being supplied from the roll 12 may be a web of conventional, uncoated or clay-coated solid bleached sulfate (SBS) paperboard, uncoated or clay-coated solid unbleached sulfate (SUS) paperboard, uncoated or clay-coated recycled paperboard, uncoated or clay-coated unbleached kraft paperboard, or any other suitable paperboard, or the like. Alternatively, the web 6 may be a web of any suitable type of paper or paper-based material, or the like. Paper-based materials, such as paper and paperboard, include cellulose. As another alternative, the web 6 may optionally be in the form of a substance that does not include cellulose.

The backside coater 16 may be in the form of any suitable backside coater. For example, the backside coater 16 may apply the liquid antimicrobial treatment 4 in any suitable manner. For example and to the extent feasible, the backside coater 16 may be a spray coater, dip coater, roll coater, rod coater, printing press, or the like, and/or any combination thereof. As one specific example and as schematically shown in FIG. 1, the backside coater 16 may be a conventional rotogravure printing press. As shown in FIG. 1, the conventional backside gravure press 16 includes an impression roller 30 and a printing cylinder 32 between which the web 6 is nipped. The antimicrobial treatment 4 is contained in, and supplied to the printing cylinder 32 from, an upwardly open container or fountain 36 of the backside press 16. A conventional doctor blade 38 is associated with the printing cylinder 32 and fountain 36 in a conventional manner.

As schematically shown in FIG. 1 by way of arrows closely associated with a dispersion chamber 40, the antimicrobial treatment 4 may be supplied from the dispersion chamber to the fountain 36 of the backside press 16, and the antimicrobial treatment may be formed in the dispersion chamber by combining at least one liquid dispersion medium 42 and at least one solute 44. In the first embodiment, the liquid dispersion medium 42 comprises a solvent, and the solvent may be water; and the solute 44 is a copper-based material, wherein the copper-based material may be one or more copper salts, and even more specifically the copper-based material may be copper sulfate. In addition and optionally, one or more other suitable additives may be added to the antimicrobial treatment 4 and/or the solute 44 may be added to any other suitable liquid dispersion medium 42. In this regard and reiterating from above, the antimicrobial treatment 4 may further include one or more other inorganic materials or salts, such as calcium hydroxide, and/or one or more organic biocides, such as isothiazolone.

As another example, the liquid dispersion medium 42 may be or may comprise any suitable conventional material (e.g., ink or other suitable coating material) that is typically coated on the backside 14 of paperboard. For example and to the extent feasible, the dispersion medium 42 may comprise pigmented coating material, ink, oil and grease resistant coating material, polymeric coating material, wax-based coating material, coating material containing fluorocarbon(s), or the like, or any suitable combination thereof. In one aspect of this disclosure, the dispersion medium 42 may comprise (e.g., may be in the form of) a conventional coating material (e.g., ink) to which one or more of the antimicrobial agents 44 discussed herein is added, so that the antimicrobial treatment 4 has a viscosity that is substantially the same as, or varies within a reasonable amount from, the viscosity of the conventional coating. Accordingly, when the antimicrobial treatment 4 has a viscosity that is substantially the same as, or varies within a reasonable amount from, the viscosity of a conventional coating, the antimicrobial treatment 4 may be applied to the backside 14 of the web 6 in substantially the same manner in which the conventional coating would be applied to the backside of the web.

Each of the one or more front coaters 26 may be in the form of any suitable front coater, and it may apply any suitable coating(s). For example, the at least one front coater 26 may be identical to, and may apply the same type of coatings as, the backside coater 16. More specifically and in accordance with the first embodiment, the one or more front coaters may each be operative for applying one or more inks onto the front side 24 of the web 6 in a conventional manner, for providing text, graphics and any other suitable images on the front side of the web.

As one specific example and as schematically shown in FIG. 1, the at least one front coater 26 may be a conventional rotogravure printing press having an impression roller 30, printing cylinder 32, fountain 36 and doctor blade 38, as discussed above. As shown in FIG. 1, the web 6 is inverted in a conventional manner so that the front coating may be applied to the front side 24 of the web 6 in a conventional manner by way of the conventional front side rotogravure printing press 26. Alternatively, the inverting of the web 6 may be omitted, for example if the front coater 26 is not the conventional type of gravure press shown in FIG. 1. As another alternative, the backside and/or front coaters 16, 26 may be any other suitable type of printers, which may include offset lithographic, flexographic, letterpress, silk screen or digital printers. As still another alternative, the web 6 may be cut into sheets before the printing, so that the sheets are serially supplied through the upstream portion of the system of FIG. 1.

As shown in FIG. 1, downstream from the coaters 16, 26, the at least one conventional converter 28 serially converts (e.g., via conventional cutting and scoring equipment, or the like) the treated web 6 (e.g., substrate) into sheets 8 of packaging material, and then the at least one conventional packaging-forming machine 29 forms the sheets 8 into the packages 10. It is optional for the converter 28 and package former 29 to be part of the same system as the coaters 16, 26. For example and at least partially reiterating from above, the treated web 6 may be wound onto a roll that is subsequently unwound and supplied to a converter 28 that is remotely located from the coaters 16, 26. Similarly, the sheets 8 may be stacked and then subsequently unstacked and supplied to a package former 29 that is remotely located from the converter 28.

As shown in FIG. 2, each of the sheets 8 (FIG. 1) may be in the form of a carton blank 8. In the example shown in FIG. 2, the carton blank 8 may be conventional, except that the carton blank includes the antimicrobial solute 44 (FIG. 1), wherein the solute typically precipitates out of the liquid antimicrobial treatment 4 coated onto the web 6 in response to evaporation of solvent(s) of the dispersion medium 42 (FIG. 1). Typically at least some of the solvent(s) of the dispersion medium 42 evaporate in at least one of the dryers 22, so that the solute 44 precipitates and, thus, becomes adhered to the web 6 (e.g., substrate). Alternatively or additionally, the antimicrobial agent, or more specifically the solute 44, may be adhered to the substrate in any other suitable manner. The precipitated solute 44 is schematically illustrated by stippling in FIG. 2.

In the example shown in FIG. 2, the blank 8 has square side panels 46 respectively foldably connected to one another by fold lines, a rectangular attachment panel or flap 48 foldably connected to the rightmost side panel by a fold line, rectangular end flaps 50 foldably connected to opposite edges of the side panels by fold lines, and cuts (e.g., slits) separating adjacent end flaps from one another. The fold lines, cuts and slits may be more generally referred to as lines of disruption. A wide variety of different types of blanks 8 and other sheets of packaging material are within the scope of this disclosure.

As schematically illustrated by stippling in FIG. 2, the precipitated solute 44 may coat (e.g., substantially coat) the entire (e.g., substantially the entire) backside of the blank 8 and/or the precipitated solute may be embedded (e.g., substantially embedded) in the paperboard of the blank. The degree to which the precipitated solute 44 may be embedded may depend upon factors such as the quantity of any sizing in the paperboard and/or the presence of any coatings that were applied to the backside 14 of the web 6 prior to the application of the liquid antimicrobial treatment 4. These and other factors, such as the concentration of the solute 44 in the antimicrobial treatment 4 and the amount of the treatment applied by the coater(s) 16 and/or 26, may be controlled so that a suitable antimicrobial amount of the precipitated solute is included in and/or coated onto the blank 8.

Further regarding the antimicrobial effectiveness of the antimicrobial treatment 4 (e.g., the precipitated solute 44 from the antimicrobial treatment) that is adhered to or otherwise carried by the blank 8, the solute may comprise copper-based material, one or more copper salts and/or copper sulfate, and the liquid antimicrobial treatment may further include one or more other additives, wherein the other additives may include one or more other inorganic materials, such as calcium hydroxide, and/or one or more organic biocides, such as isothiazolone. Accordingly, one or more of these other additives may coat (e.g., substantially coat) the backside of the blank 8 and/or be embedded (e.g., substantially embedded) in the paperboard of the blank. Accordingly, it is also within the scope of this disclosure to control the relative proportions of the copper-based material and any other additives in a manner that seeks to control the antimicrobial effectiveness of the sheet/blank 8 and package/carton 10.

Figure 3:
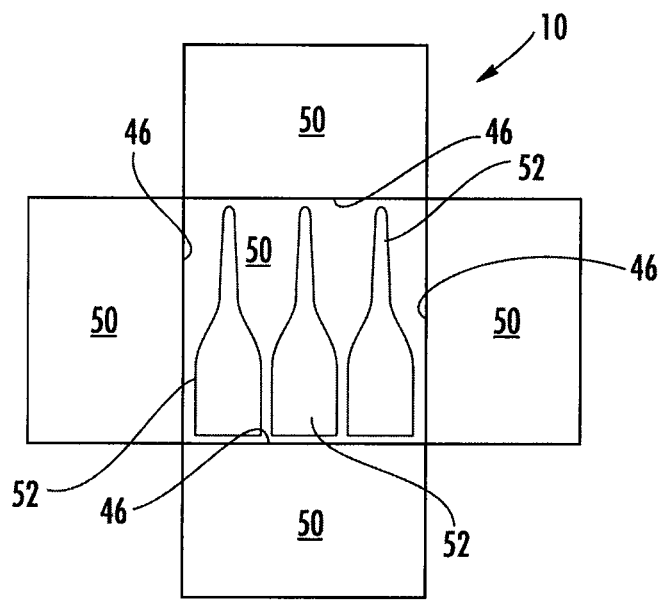
FIG. 3 is a schematic end elevation view of a carton erected from the blank of FIG. 2, wherein an end of the carton is open, and the carton contains inner containers that may contain a food product, in accordance with the first embodiment.

The blanks 8 may be erected in a conventional manner, such as by folding along the fold lines of the blank and applying adhesive material to the attachment and end flaps 48, 50, wherein the erecting may be performed by the package former 29 and/or manually. As shown in FIG. 3, the blank 8 of FIG. 2 has been erected into the carton 10, and one or more conventional inner containers 52 that contain food product in the form of a liquid beverage are positioned in the interior of the open-ended carton, wherein the open end flaps 50 will subsequently be closed to close the open end of the carton. The inner containers 52 may be more generally referred to as articles or contents.

The beverage (e.g., juice) is typically hermetically sealed in the conventional inner containers 52. The inner containers 52 are schematically shown in FIG. 3 as being in the form of pouches. The pouches 52 may be formed of polymeric film that may optionally be metalized and/or colored. Notwithstanding, under some circumstances (e.g., adverse conditions), beverage may leak from one or more of the containers 52 within the carton 10, such as when the carton is in a closed configuration. In the first embodiment, the precipitated solute 44 from the treatment 4, optionally in combination with one or more other additives from the treatment 4, are adhered to or otherwise carried by the blank 8 in a configuration and amount that seeks to inhibit (e.g., prevent or substantially prevent) such leaking beverages or other products from causing microorganisms to grow on and/or in the material of the carton 10. As one possible example, at least some of the precipitated solute 44 carried by the carton 10 may advantageously become dispersed in any leaking beverage, so that microorganisms are at least discouraged or substantially prevented from growing in the resulting beverage-based dispersion.

The blank 8 and carton 10 shown in FIGS. 2 and 3 provide very basic examples of the myriad of different types of blanks and cartons that are within the scope of this disclosure. For example, a variety of different blanks are within the scope of this disclosure, such as, but not limited to, blanks for being erected into any suitable type of conventional carton structures, which may include boxes, trays, sleeves, wraparound carriers, basket carriers, and any other suitable types of packages. In addition, the paper-based packaging materials of this disclosure may be formed into any suitable type of convention package structures such as, but not limited to, tubes and any other suitable packages formed by wrapping and/or in any other suitable manner.

A second embodiment of this disclosure is like the above-described first embodiment, except for variations noted and variations that will be understood by those of ordinary skill in the art. In the second embodiment, the antimicrobial treatment 4 may be applied or otherwise incorporated into the web 6 (e.g., adherence between the web and the antimicrobial agent 44 may be caused) at any appropriate time prior to (e.g., upstream from) any coaters 16, 26. As a more specific example, the antimicrobial treatment may be applied or otherwise incorporated into the web 6 at any suitable time while the web is being manufactured by a papermaking machine.

Conventional sections of a conventional papermaking machine (not shown) include a wet end section and a calender section. For example, the antimicrobial treatment 4, or a portion thereof, may be applied or otherwise incorporated into the precursor of the web 6 in the wet end section and/or the calender section of the papermaking machine. In the wet end section, one or more of the above-discussed antimicrobial agents may be included in the slurry of plant fibers (e.g., wood pulp) that are contained in the conventional headbox, or the like, of the wet end section. Optionally, it may be preferred for the antimicrobial agents in the form of salts not to be incorporated into the wet end section, because of corrosions issues that may be associated with the salt.

Alternatively or in addition, the antimicrobial treatment, or a portion thereof, may be applied to the surface of (and thereby be attached or otherwise incorporated into) the precursor of the web 6 in the calender section of the papermaking machine. In this regard, the antimicrobial treatment, or a portion thereof, may be included with one or more sizing agents (e.g., resins, glue, or starch) that are applied to the surface of the precursor web in the calender section, such as by way of roll applicator(s) (e.g., flooded nip) and/or any other suitable applicator(s). For example, it is conventional for the surface of a precursor web to be treated with a dispersion comprising water and starch, wherein this treatment occurs in a nipping calender system. In accordance with one aspect of this disclosure, the antimicrobial treatment 4, or a portion thereof, may be included in the dispersion associated with (e.g., applied to the precursor web at) the nipping calender system in the dry end of the papermaking machine.

Alternatively and/or in addition, the antimicrobial treatment 4, or a portion thereof, may be applied to the surface of the web 6, or a precursor of the web, by way of any other suitable coating machine(s). For example, the antimicrobial treatment, or a portion thereof, may be applied by such coating machine(s) as part of a filler composition that may include calcium carbonate, china clay, starch, styrene-butadiene latex and/or any other suitable material(s).

A fold line may be any substantially linear, although not necessarily straight, form of weakening that facilitates folding therealong. More specifically, but not for the purpose of narrowing the scope of the present invention, fold lines include: a score line, such as lines formed with a blunt scoring knife, or the like, which creates a crushed portion in the material along the desired line of weakness; a cut that extends partially into a material along the desired line of weakness, and/or a series of cuts that extend partially into and/or completely through the material along the desired line of weakness; and various combinations of these features. In situations where cutting is used to create a fold line, typically the cutting will not be overly extensive in a manner that might cause a reasonable user to incorrectly consider the fold line to be a tear line or other line of disruption.

The above examples are in no way intended to limit the scope of the present invention. It will be understood by those skilled in the art that while the present disclosure has been discussed above with reference to exemplary embodiments, various additions, modifications and changes can be made thereto without departing from the spirit and scope of the invention, some aspects of which are set forth in the following claims.

What is claimed is:

1. A package comprising a carton and a plurality of beverage containers, the carton comprising:
    a substrate comprising paperboard, the substrate extending at least partially around an interior of the carton, the substrate comprising an interior surface facing the interior of the carton; and
    a coating adhered to at least a portion of the interior surface of the substrate so that the coating extends at least partially around the interior of the carton, the coating comprising an antimicrobial agent that is at least partially exposed to the interior of the carton on an innermost surface of the carton, the antimicrobial agent comprising copper salt;
    wherein the plurality of beverage containers are disposed in the interior of the carton and a beverage that has leaked from at least one beverage container of the plurality of beverage containers is in the interior of the carton, and the beverage is at least partially in contact with the coating on the innermost surface of the carton so that the copper salt is at least partially dispersed in the beverage that has leaked from the at least one beverage container in the interior of the carton.

2. The packaging material of claim 1, wherein the antimicrobial agent further comprises an inorganic salt.

3. The packaging material of claim 1, wherein the copper salt comprises copper sulfate.

4. The packaging material of claim 1, wherein:
    the copper salt is a first inorganic material, and
    the antimicrobial agent further comprises a second inorganic material.

5. The packaging material of claim 4, wherein the second inorganic material is a salt.

6. The packaging material of claim 4, wherein the second inorganic material is calcium hydroxide.

7. The packaging material of claim 1, further comprising a coating adhered to the outer surface of the substrate, wherein the coating adhered to the outer surface of the substrate comprises an antimicrobial agent.

8. The packaging material of claim 7, wherein the coating adhered to the outer surface of the substrate further comprises pigment.

9. The packaging material of claim 1, wherein the antimicrobial agent further comprises an organic biocide.

10. The packaging material of claim 9, wherein the organic biocide comprises isothiazolone.

11. The packaging material of claim 1, wherein the coating further comprises pigment.

12. A package comprising a carton and a plurality of beverage containers, the carton comprising:
a substrate comprising paperboard, the substrate extending at least partially around an interior of the carton, the substrate comprising an interior surface facing the interior of the carton; and
a coating adhered to at least a portion of the interior surface of the substrate so that the coating extends at least partially around the interior of the carton, the coating comprising an antimicrobial agent that is at least partially exposed to the interior of the carton on the innermost surface of the carton, the antimicrobial agent comprising copper sulfate;
wherein the plurality of beverage containers are disposed in the interior of the carton and a beverage that has leaked from at least one beverage container of the plurality of beverage containers is in the interior of the carton, and the beverage is at least partially in contact with the coating on the innermost surface of the carton so that the copper sulfate is at least partially dispersed in the beverage that has leaked from the at least one beverage container in the interior of the carton.

13. The packaging material of claim 12, wherein:
the copper sulfate is a first inorganic material, and
the antimicrobial agent further comprises a second inorganic material selected from the group consisting of a salt and calcium hydroxide.

14. The packaging material of claim 12, wherein the antimicrobial agent further comprises an organic biocide.

15. The packaging material of claim 12, wherein the coating further comprises pigment.

16. The packaging material of claim 12, further comprising a coating adhered to the outer surface of the substrate, wherein the coating adhered to the outer surface of the substrate comprises an antimicrobial agent.

17. The packaging material of claim 16, wherein the coating adhered to the outer surface of the substrate further comprises pigment.

18. A method, comprising:
at least partially providing a packaging material, the packaging material comprising a substrate and a coating adhered to a first surface of the substrate, wherein the substrate comprises cellulose, the coating comprises an antimicrobial agent, the antimicrobial agent comprises copper salt, and the packaging material is in the form of a carton blank;
then forming the carton blank into a carton so that
the packaging material extends at least partially around an interior space of the carton,
the first surface faces toward the interior space, and
a second surface of the substrate faces away from the interior space, wherein the first and second surfaces of the substrate are opposite from one another;
loading a plurality of beverage containers at least partially into the interior space; and
dispersing the copper salt in a beverage that has leaked from at least one beverage container of the plurality of beverage containers in the interior space.

19. The method of claim 18, wherein:
the at least partially providing is comprised of printing the coating on the first side of the substrate, and
the coating further comprises pigment.

20. The method of claim 18, wherein the coating is an ink that comprises the antimicrobial agent.

21. The method of claim 18, wherein:
the substrate comprises paperboard, and
the copper salt comprises copper sulfate.

* * * * *